United States Patent [19]

Nott et al.

[11] Patent Number: 6,013,093

[45] Date of Patent: Jan. 11, 2000

[54] BLOOD CLOT FILTERING

[75] Inventors: Sepideh H. Nott, Newton; Hannah S. Kim, Boxborough; Naroun Suon, Lynn; David L. Sandock, deceased, late of Littleton, all of Mass., by Edna Ruth Sandock, executrix

[73] Assignee: Boston Scientific Corporation, Natick, Mass.

[21] Appl. No.: 08/849,392

[22] PCT Filed: Nov. 28, 1995

[86] PCT No.: PCT/US95/15365

§ 371 Date: Nov. 10, 1997

§ 102(e) Date: Nov. 10, 1997

[87] PCT Pub. No.: WO96/17634

PCT Pub. Date: Jun. 13, 1996

[51] Int. Cl.[7] .................................................. A61B 17/00
[52] U.S. Cl. ............................................................ 606/200
[58] Field of Search ........................... 606/200, 191–199; 604/104; 623/1, 11, 12, 13

[56] References Cited

U.S. PATENT DOCUMENTS

| | | |
|---|---|---|
| 3,540,431 | 11/1970 | Mobin-Uddin et al. . |
| 3,952,747 | 4/1976 | Kimmell, Jr. . |
| 4,425,908 | 1/1984 | Simon . |
| 4,494,531 | 1/1985 | Gianturco . |
| 4,619,246 | 10/1986 | Molgaard-Nielsen et al. . |
| 4,643,184 | 2/1987 | Mobin-Uddin . |
| 4,655,771 | 4/1987 | Wallsten . |
| 4,688,553 | 8/1987 | Metals . |
| 4,727,873 | 3/1988 | Mobin-Uddin . |
| 4,781,177 | 11/1988 | Lebigot . |
| 4,793,348 | 12/1988 | Palmaz . |

(List continued on next page.)

FOREIGN PATENT DOCUMENTS

| | | |
|---|---|---|
| 0 348 295 A1 | 12/1989 | European Pat. Off. . |
| 0 430 848 A1 | 5/1991 | European Pat. Off. . |
| 0 437 121 A2 | 7/1991 | European Pat. Off. . |
| 0 462 008 A1 | 12/1991 | European Pat. Off. . |
| 0 472 334 A1 | 2/1992 | European Pat. Off. . |
| 2 649 884 | 1/1991 | France . |
| 835447 | 5/1979 | Russian Federation . |
| 1103868 | 7/1983 | Russian Federation . |
| 9559912 | 2/1988 | Russian Federation . |
| 2 200 848 | 8/1988 | United Kingdom . |
| 2 200 848 | 2/1991 | United Kingdom . |
| WO 91/04716 | 4/1991 | WIPO . |
| WO 91/11972 | 8/1991 | WIPO . |
| WO 95/09567 | 4/1995 | WIPO . |
| WO 95/27448 | 10/1995 | WIPO . |

OTHER PUBLICATIONS

Kraimps et al., "Conical Endocaval Filters with Metalltic Struts: Search for a New Model", Mar. 1992, Ann. Vasc. Surg., 6:99–110.

Kraimps et al., "Optimal Central Trapping (OPCETRA) Vena Caval Filter: Results of Experimental Studies", Nov. 1992, J. Vasc. and Inter. Rad., 3:697–701.

*Primary Examiner*—Michael Buiz
*Assistant Examiner*—Vikki Trinh
*Attorney, Agent, or Firm*—Hoffmann & Baron, LLP

[57] ABSTRACT

This invention is a blood clot filter having an anchoring portion (402) which includes a generally cylindrical self-expanding body. A generally conical filtering portion (400) is axially aligned with the cylindrical body (402), has an open proximal end (406) coupled to a distal end of the anchoring portion, and an apical distal end (404). In a preferred embodiment, the filter portion (400) is formed from strands (410) of resilient material that extend from the apical distal end (404) to the open proximal end (406). The strands (410) form twisted pairs (408) that converge at the apical distal end (404). The strands (410) diverge from the twisted pairs (408) in crossing paths to form a pattern of open filtering cells (A)(B)(C). The filter also has hooks (413) coupled to the anchoring portion (402) and formed from compliant material having an original shaped that bends under stress yet returns to its original shaped when unstressed.

45 Claims, 9 Drawing Sheets

U.S. PATENT DOCUMENTS

| | | |
|---|---|---|
| 4,817,600 | 4/1989 | Herms et al. . |
| 4,830,003 | 5/1989 | Wolff et al. . |
| 4,832,055 | 5/1989 | Palestrant . |
| 4,856,516 | 8/1989 | Hillstead . |
| 4,873,978 | 10/1989 | Ginsburg . |
| 4,943,297 | 7/1990 | Saveliev et al. . |
| 4,954,126 | 9/1990 | Wallsten . |
| 4,957,501 | 9/1990 | Lahille et al. . |
| 4,969,891 | 11/1990 | Gewertz . |
| 4,990,156 | 2/1991 | Lefebvre . |
| 5,059,205 | 10/1991 | El-Nounou et al. . |
| 5,061,275 | 10/1991 | Wallsten et al. . |
| 5,071,407 | 12/1991 | Termin et al. . |
| 5,108,418 | 4/1992 | Lefebvre . |
| 5,108,419 | 4/1992 | Reger et al. . |
| 5,133,733 | 7/1992 | Rasmussen et al. . |
| 5,135,516 | 8/1992 | Sahatjian et al. . |
| 5,152,777 | 10/1992 | Goldberg et al. . |
| 5,160,342 | 11/1992 | Reger et al. . |
| 5,190,546 | 3/1993 | Jervis . |
| 5,221,261 | 6/1993 | Termin et al. . |
| 5,224,953 | 7/1993 | Morgentaler . |
| 5,300,086 | 4/1994 | Gory et al. . |
| 5,304,121 | 4/1994 | Sahatjian . |
| 5,304,200 | 4/1994 | Spaulding . |
| 5,324,304 | 6/1994 | Rasmussen . |
| 5,329,942 | 7/1994 | Gunther et al. . |
| 5,344,427 | 9/1994 | Cottenceau et al. . |
| 5,370,657 | 12/1994 | Irie . |
| 5,375,612 | 12/1994 | Cottenceau et al. . |
| 5,382,261 | 1/1995 | Palmaz . |
| 5,405,377 | 4/1995 | Cragg ................................ 623/1 |
| 5,476,508 | 12/1995 | Amstrup ............................ 623/1 |
| 5,522,822 | 6/1996 | Phelps et al. .................. 606/191 X |
| 5,549,626 | 8/1996 | Miller et al. ...................... 606/200 |
| 5,683,411 | 11/1997 | Kavteladze et al. ............... 606/200 |
| 5,709,704 | 1/1998 | Nottt et al. ....................... 606/200 |

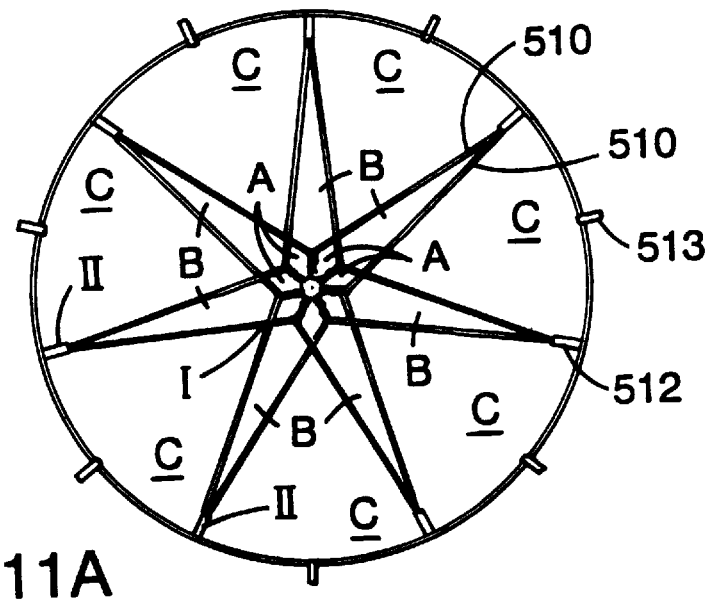
FIG. 11A
FIG. 11
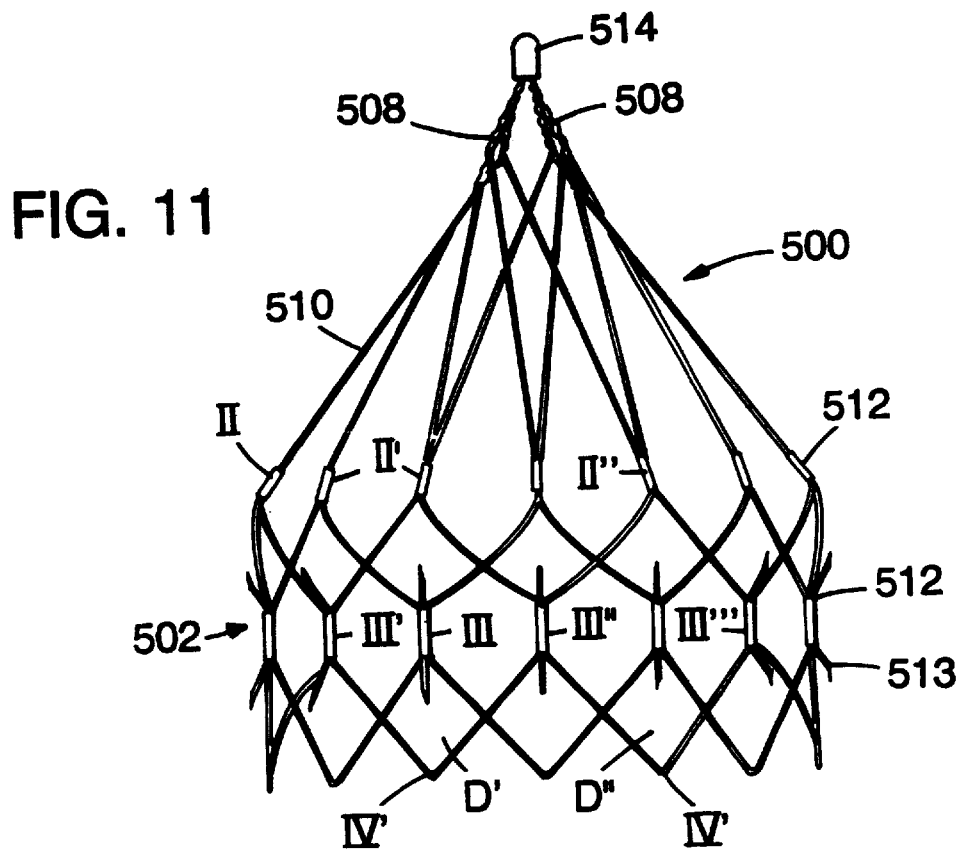

BLOOD CLOT FILTERING

FIELD OF THE INVENTION

This invention relates to blood clot filtering.

BACKGROUND

Blood clots that form in the lower part of the body may migrate to the heart and may be subsequently pumped to the lungs. Small clots can be absorbed by the body without adverse effect. However, larger clots can interfere with the oxygenation of blood (e.g., on the order of 3 mm in diameter and 10–30 cm in length) and can possibly cause shock or sudden death.

Many transvenous filtering devices have been developed for installation in the vena cava to prevent especially large clots from reaching the lungs. These filters have fine wires positioned in the blood flow to catch and hold clots for effective lysing in the blood stream. Some of these devices are inserted into the vena cava by dissecting the internal jugular vein in the neck or the femoral vein in the groin, inserting a metallic capsule containing a filtering device to the proper position in the vena cava, and releasing the filtering device into the vena cava. More recently, filters have been designed for percutaneous introduction into the vasculature.

SUMMARY OF THE INVENTION

In one aspect, the invention features a filter sized and constructed to be compressed and passed through the vasculature of a patient to be anchored against an inner wall surface of a blood vessel for capturing blood clots in a blood stream passing therethrough. The filter comprises: an anchoring portion comprising a generally cylindrical self-expanding body formed from resilient material, the generally cylindrical body having proximal and distal ends and defining an axial direction and having a structure of variable size diameter expandable from a low-profile compressed condition to a larger profile expanded condition, wherein the resilient material urges the generally cylindrical body to radially expand and to thereby apply anchoring radial force against the inner wall surface of the blood vessel; and a generally conical filtering portion axially aligned with the generally cylindrical body having an open proximal end coupled to the distal end of the anchoring portion and having an apical distal end, the anchoring portion and the filtering portion being substantially non-overlapping to achieve a low profile compressed condition for delivery of the filter through the vasculature.

Embodiments of the invention may include one or more of the following features. The generally conical filtering portion is preferably formed from a plurality of elongated strands arranged to form a generally conical structure to guide blood clots in the blood stream flowing therepast to the apical distal end of the generally conical filtering portion for lysing. The elongated strands forming the generally conical filtering portion are constructed and arranged to maintain a generally conical shape whether the anchoring portion is in a compressed condition or an expanded condition. The anchoring portion and the filtering portion are preferably constructed and arranged so that the proximal end of the filtering portion conforms to the shape of the cylindrical body of the anchoring portion. The elongated strands are preferably fixedly attached to one another only at the apex of the generally conical filtering portion. The elongated strands may be formed from nitinol (nickel-titanium alloy), plastically deformable material, temperature-sensitive shape memory material with a transition temperature around body temperature, or elastic material having a core formed from radiopaque material. The filter may be coated with a drug for in vivo compatibility. The resilient elongated strands preferably extend from the proximal end of the anchoring portion to the distal apical end of the filtering portion.

The elongated strands of the filtering portion may define a plurality of neighboring filtering cells. According to one embodiment, the neighboring filtering cells are preferably loosely coupled together at the respective areas of contact between neighboring cells. The neighboring cells are preferably coupled together by helical twisting of portions of respective elongated strands of neighboring cells. The portion of the twisted-together elongated strands are preferably capable of slight mutual separation to accommodate changes in the shapes of the cells from the expanded to the compressed conditions.

According to another embodiment, the strands cross one another and are slidably movable relative to each other at their crossing regions.

The generally conical filtering portion preferably comprises at least two rings of cells, wherein the cells of each ring are of substantially equal size and are spaced substantially the same distance from the apical distal end of the filtering portion. The size of the cells in the rings is preferably smaller for cells closer to the apical distal end of the filtering portion than for cells located a greater distance from the apical distal end of the filtering portion.

The elongated strands may be twisted together in twisted groups of strands that converge at the apical distal end of the filter portion. The strands forming each twisted group may diverge from the twisted group and extend in paths therefrom to the open proximal end of the filter portion. Preferably, the twisted groups are twisted pairs of strands that diverge in either straight paths or spiralling paths that cross one another.

The elongated strands of the filtering portion may be spirally arranged with respect to one another from the proximal end of the filtering portion to the apical distal end of the filtering portion.

The elongated strands are preferably selected to have sufficient rigidity to maintain the generally conical shape of the filtering portion.

The self-expanding anchoring portion preferably comprises a ring of neighboring cells. The cells of the anchoring portion are preferably self-expanding. The cells of the anchoring portion preferably cooperate to urge the generally cylindrical body of the anchoring portion to radially expand from a compressed condition to an expanded condition. The neighboring cells of the anchoring portion are preferably fixedly coupled together at respective areas of contact. The cells of the anchoring portion are preferably formed from one or more resilient elongated strands. When the generally cylindrical body is in a compressed condition, the cells of the anchoring portion are preferably elongated in the axial direction.

In another general aspect, the invention features a blood clot filter comprising: an anchoring portion formed from resilient material having proximal and distal ends and having a generally circular transverse cross-section defining an axial direction, the anchoring portion further having a structure of variable size diameter expandable from a low-profile compressed condition to a larger profile expanded condition, wherein the resilient material urges the anchoring portion to radially expand and to thereby apply anchoring radial force against the inner wall surface of the blood vessel; a filtering portion axially aligned with the generally cylindrical body having an open proximal end coupled to the distal end of the anchoring portion; and one or more hooks fixedly coupled to the anchoring portion formed from compliant material having an original shape that bends under stress yet returns to its original shape when unstressed, said one or more hooks respectively tending to project from the anchoring portion at an acute angle with respect to the axial direction for engagement with a vessel wall, the one or more hooks further being deflectable toward the anchoring portion for achieving a low-profile.

Embodiments of the invention may include one or more of the following features. The hooks are preferably formed from nitinol. The hooks preferably preferentially bend toward and away from the vessel wall engaging portion. The hooks are preferably formed from flat nitinol wire having a width dimension and having a thickness dimension substantially smaller than the width dimension for achieving preferential bending; the flat nitinol wire being oriented so that the thickness dimension of the flat nitinol wire coincides with a radial direction of the anchoring portion. The hooks preferably preferentially bend toward and away from the vessel wall engaging portion.

Among the advantages of the present invention are the following. Because the anchoring portion and the filtering portion have constructions that are optimally designed for their respective functions, the filter can have a low profile while providing a robust design that can readily accommodate different vessel sizes. Furthermore, the anchoring portion serves to center the filtering portion. The filtering portion of the filter should have a small enough capture cross-section to prevent large clots from passing therethrough. This requires a sufficient amount of filtering material (e.g., elongated strands) to reduce the capture cross-section. Since the conical filtering portion according to the present invention does not also have to support the filter in the vessel, smaller-sized elements can be used to form the filter to achieve a lower profile. The profile of the present invention can be made small, while providing substantially the same anchoring force and substantially the same filtering efficiency as, e.g., a GREENFIELD® 24 Fr stainless steel filter (available from Medi-Tech, Inc. of Watertown, Mass., U.S.A.). The filter designs minimally disturb blood flow, while achieving a desirable level of filtering efficiency. Since the sizes of the cells of the filtering portion decrease from the proximal end to the distal end, larger cells are positioned near the vessel walls where the flow velocity is relatively low and smaller cells are positioned in the central region of the vessel where the flow velocity is highest and where the most effective clot lysing occurs. Without being limited to a particular theory, it is believed that clots traveling with lower velocity do not pass through the larger size cells in the periphery of the conical filtering portion, but are instead guided to the apical distal end of the filtering portion. Clots traveling with higher velocities in the central region of the vessel, which may otherwise pass through the larger size peripheral cells, are caught in the smaller size cells located at the distal end of the filtering portion. Because the radial force against the vessel wall is distributed along a length of the vessel wall a filter according to the present invention offers higher resistance to migration as well as less trauma to the vessel wall.

Other features and advantages will become apparent from the following description and from the claims. For example, the invention features a process for making a blood clot filter and a method for treating a patient by implanting a blood clot filter into a blood vessel of the patient.

BRIEF DESCRIPTION OF THE DRAWING

FIGS. 6 and 6A are diagrammatic side and end views of a filter.

FIGS. 11 and 11A are diagrammatic side and end views of a filter in an expanded condition.

DETAILED DESCRIPTION OF THE INVENTION

Figure 1A:
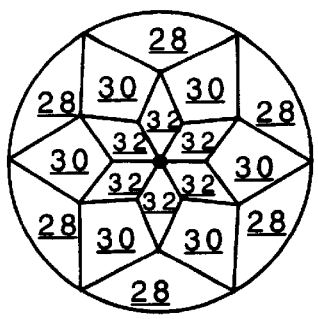
FIGS. 1 and 1A are diagrammatic side and end views of a filter in an expanded condition.

Referring generally to FIGS. 1–1C and 2–2B, a blood clot filter 10 includes a generally cylindrical anchoring portion 12 and a generally conical filtering portion 14 terminating at a closed, distal apical end 16. The cylindrical portion uniformly exerts an outward radial force to anchor the filter in a blood vessel (e.g., the vena cava) in which it is disposed; the exerted force being sufficient to prevent migration of the filter in the vessel. The generally cylindrical shape of the anchoring portion conforms to the inner wall surface of a blood vessel and properly centers the filtering portion within the vessel. The filtering portion provides a conical meshwork across the blood vessel to catch and retain clots in the blood stream.

Cylindrical portion 12 is formed by a ring 18 of circumferentially arranged cells 20. Filtering portion 14 is formed by a series of three rings (22, 24, 26) of relatively loosely connected cells (28, 30, 32, respectively). The size of the cells forming the rings of the filtering portion increases from apical end 16 of the filtering portion to the proximal end 34 of the filtering portion, which is adjacent the distal end 36 of the anchoring portion.

Figure 1:
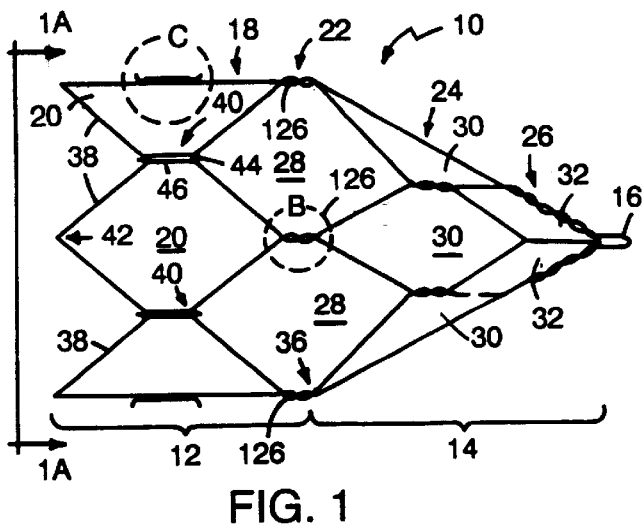
Figure 1B:
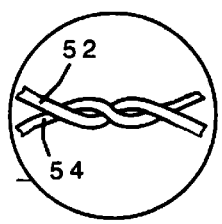
FIGS. 1B and 1C are enlarged views of respective portions of the filter shown in FIG. 1.
Figure 1C:
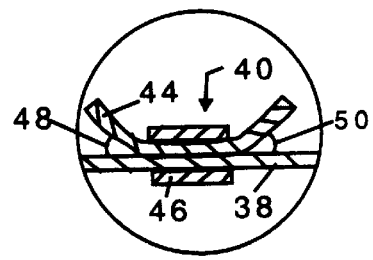

Cells 20 of the cylindrical portion of the filter are defined by elongated strands 38 of resilient material (e.g., nitinol wire). Neighboring cells are fixedly joined together at respective regions of contact 40, e.g., by spot welding, as described in detail below. Fixed regions of contact 40 enable cells 20 in ring 18 to cooperate to urge the anchoring portion into an expanded condition (FIGS. 1–1B). The fixed regions of contact 40 also prevent the elongated strands forming cells 20 from rotating about each other, which might cause hinging and locking between the cells in a manner distorting the cylindrical shape of the anchoring portion. In a compressed condition (FIGS. 2–2B) the longitudinal length of cylindrical anchoring portion 12 increases.

Conical filtering portion 14 is constructed from a series of rings (22, 24, 26) of relatively loosely coupled cells in a manner preserving its generally conical shape, whether the filter is in a compressed condition or an expanded condition. The filtering portion does not need to provide anchoring radial force. However, the material substance forming the conical structure has sufficient structural integrity to prevent large clots in the blood flow from displacing the filtering structure. The size of the cells in the filtering portion are selected to minimally disturb the blood flow (which would otherwise encourage occlusion of the vessel), while still achieving a desired level of blood clot filtering.

In the embodiment shown in FIGS. 1–1C and 2–2B, the cells forming the filtering portion are coupled together by helically twisting together respective portions of the elongated strands defining neighboring cells. This coupling permits some rotation about the joints in a manner that preserves the generally conical shape of the filtering portion, whether the filter is in a compressed condition or an expanded condition.

Figure 2A:
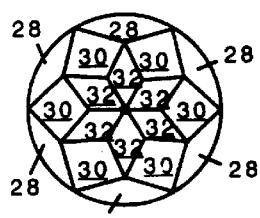
FIGS. 2 and 2A are diagrammatic side and end views of a filter in a compressed condition.
Figure 2:
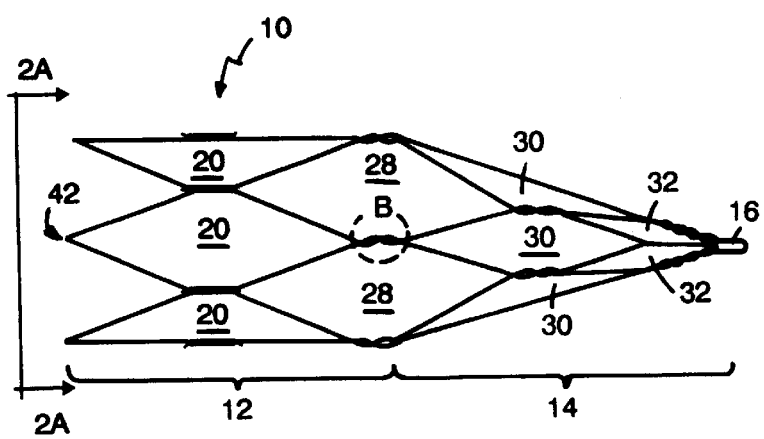
Figure 2B:
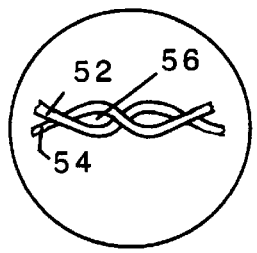
FIG. 2B is an enlarged view of a portion of the filter of FIG. 2.

Comparing FIGS. 1B and 2B, in the expanded condition (FIG. 1B), the twisted wire portions 52, 54, coupling neighboring cells in the filtering portion of the filter, are tightly wrapped about each other. However, in a compressed condition (FIG. 2B), wire portions 52, 54 move away from (and rotate about) one another to form gaps 56. This rotation or hinging prevents the build-up of internal forces within the filtering portion, which could cause the filtering portion to bow outward into a hemispherical shape, which would result in less effective blood clot filtering.

Referring back to FIG. 1C, a hook 44 formed from a section of flat nitinol wire is disposed within a tube 46 (e.g., a hypotube) and mounted at regions of contact 40 between neighboring cells in ring 18, which forms the cylindrical portion of the filter. A central region of hook 38 is mounted at regions of contact 40. Hook 44 is bent at its proximal and distal ends to respectively form acute angles 48, 50 with respect to the longitudinal axis of the cylindrical portion. The bent ends of hook 44 are oriented in divergent direction to prevent migration of the filter in proximal and distal directions. The nitinol hooks easily bend to conform to the shape of the cylindrical surface of the anchoring portion to achieve a low profile for delivery of the filter. When the filter is released into a blood vessel, the hooks return to their bent shape for engaging an inner wall surface of the vessel. Fewer hooks may be used (e.g., three hooks symmetrically disposed about anchoring portion 12 may be used) to achieve a lower profile for delivery of the filter.

In a presently preferred embodiment designed for filtering blood clots in a vena cava of about 28 mm diameter, cylindrical portion 12 includes six cells formed from nitinol wire of 0.002–0.01 inch diameter, and preferably 0.008 inch diameter (e.g., nitinol with an $A_f$ between $-10°$ C. and $+5°$ C. and constructed so that after drawing the wire has a tensile strength of about 250,000 psi to 300,000 psi, available from Shape Memory Applications of Sunnyvale, Calif., U.S.A.). Each cell in the anchoring portion has four side portions about 13 mm in length. Filter 10 is collapsible to a diameter of 0.08 inch (about 6 Fr). The anchoring portion has an expanded outer diameter of 30–31 mm.

The filtering portion includes three rings of cells of decreasing size from the proximal end 34 to the distal apical end 16. Each of the proximalmost cells in the filtering portion has four side portions: two proximal side portions about 13 mm in length and two distal side portions about 15 mm in length. Each of the intermediate cells in the filtering portion has four side portions: two proximal side portions about 15 mm in length and two distal side portions about 11 mm in length. Each of the distalmost cells of the filtering portion has four sides portions: two proximal side portions about 11 mm in length and two distal side portions about 9 mm in length. The total length of the filter in the expanded condition is about 60 mm, with the filtering portion being about 32–34 mm in length and the anchoring portion being about 26–28 mm in length. Six hooks 44 are symmetrically disposed about the anchoring portion at each of the fixed regions of contact 40. Hooks 44 are made from flat nitinol wire about 5 mm in length, about 0.5 mm in width and about 0.05–0.15 mm thick.

Figure 3:
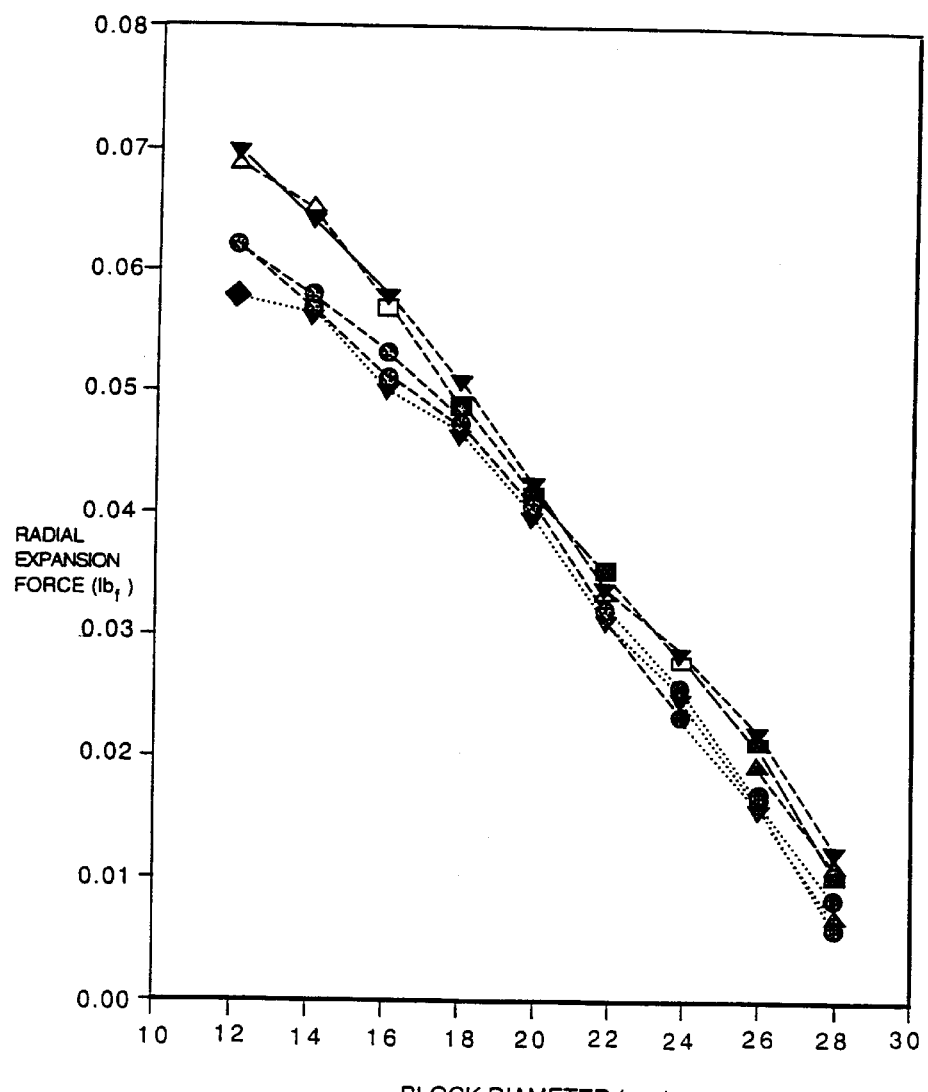
FIG. 3 is a plot of radial expansion force provided by a filter as a function of the outer diameter of the filter.

Referring to FIG. 3, the outward radial expansion forces respectively exerted by six different filters of the type shown in FIGS. 1–1C and 2–2B are plotted as a function of the outer diameter of cylindrical portion 12. The measured filters were designed with the specifications recited above. The exerted force generally varies linearly with the diameter of the anchoring portion, with the highest forces being exerted when the filter is in the lower profile conditions (i.e., most compressed). Force levels of 0.01–0.07 pounds are generally acceptable for a typical vena cava of 12–28 mm diameter. Much higher force levels may cause the filter to undesirably distort the shape of the vena cava. Also, much lower force levels would not securely anchor the filter in the vena cava and the filter may be displaced.

The number of cells in the anchoring portion and in the filtering portion may be varied to achieve larger sizes or higher forces. For example, to accommodate a so-called "mega-cava" having a diameter of up to 40 mm, the expanded outer diameter of the filter should be selected to be about 42–44 mm and the number of cells in the anchoring portion should be appropriately increased (e.g., nine cells could be used) to achieve proper outward radial force exertion to anchor the filter in the vena cava without migrating or traumatizing the vessel. Instead of increasing the number of cells, the thickness of the wire used to form the cells could be suitably increased to provide the proper amount of anchoring force. Alternatively, the exerted radial force may be increased by providing additional welds at the distal end 36 (FIG. 1) of the anchoring portion at locations 126. This increases the structural integrity of each cell 20, providing higher spring force under compression. The exerted radial force may alternatively be increased by changing the wire alloy or the degree of cold work.

Figure 3A:
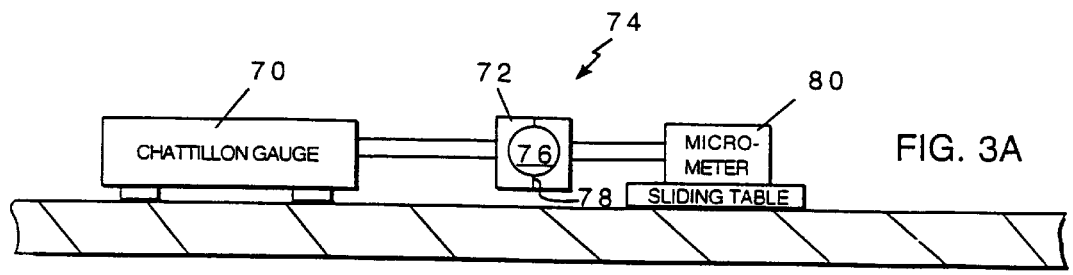
FIG. 3A is a diagrammatic side view of a system for measuring the radial force exerted by a filter as a function of the outer diameter of the filter.

Referring to FIG. 3A, the outward radial force exerted by a filter was measured using a force gauge 70 (e.g., a Chattillon gauge) attached to one half 72 of a solid block 74 through which cylindrical hole 76 of a preselected diameter is disposed. Block 74 was cut in half through a plane containing the longitudinal axis of cylindrical hole 76. A filter to be measured was placed in hole 76. A micrometer 80 attached to the other half 82 of block 74 was used to close the gap between the two halves of block 74. The force exerted by the filter was measured as a function of filter diameter by performing the measurement with a series of blocks with different preselected diameters.

Figure 4A:
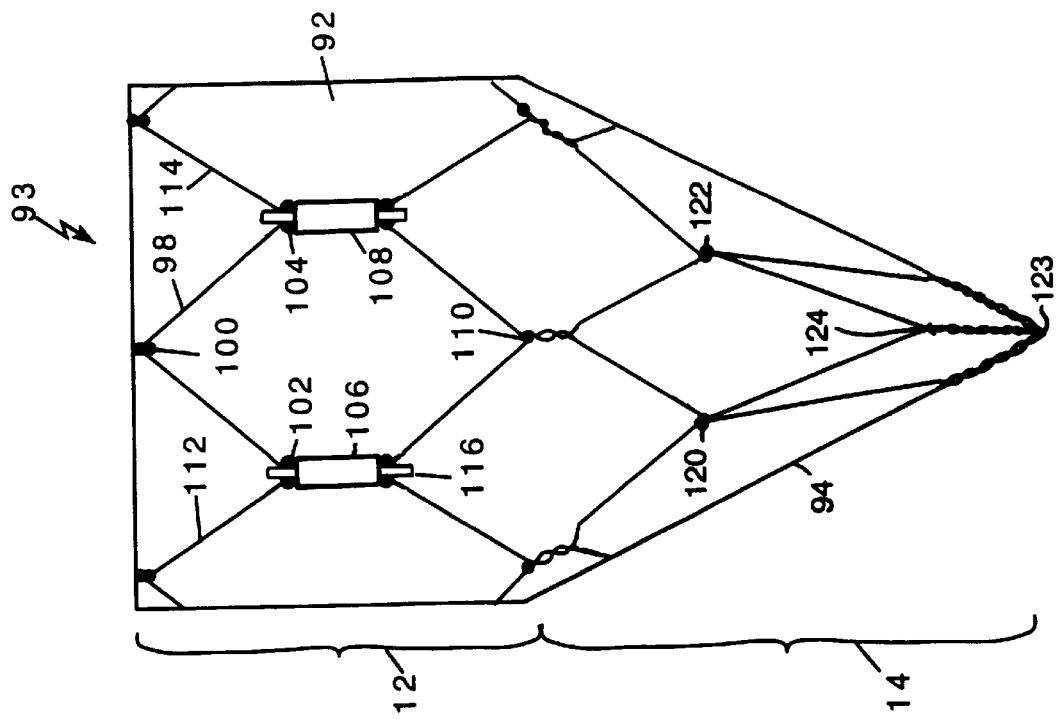
FIGS. 4-4A are diagrammatic side views of a filter and forming mandrels at different stages in a process for fabricating the filter shown in FIGS. 1–1b and 2–2B.
Figure 4:
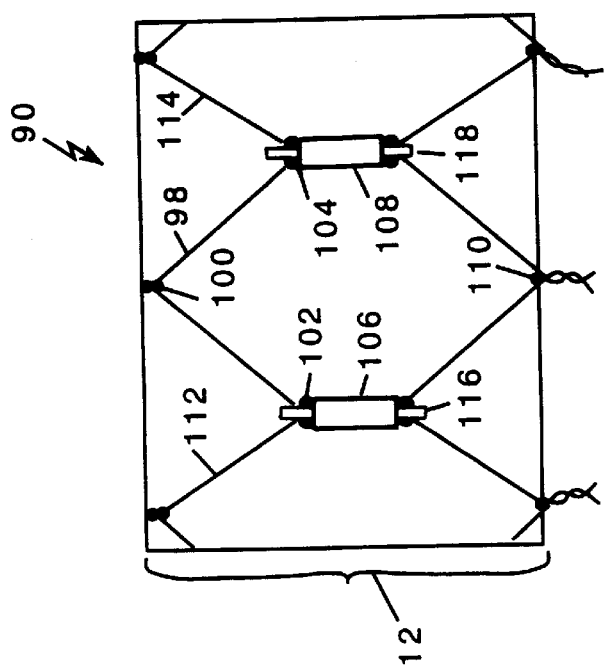

Referring to FIGS. 4 and 4A, in a process for fabricating a filter 10, a cylindrical thermally conductive mandrel 90 (e.g., formed from copper) is sized and constructed to conform to the desired filter size and shape. Mandrel 90 includes a plurality of anchoring pins protruding from its outer surface in a pattern corresponding to the desired cellular pattern for the filter.

As shown in FIG. 4, the process for fabricating the anchoring portion of the filter includes the following steps. A wire strand 98 is bent around an anchoring pin 100 to form the proximal end of anchoring portion 12 of the filter. The two ends of wire strand 98 are pulled divergently downward to pins 102, 104 and through respective hypotubes 106 and 108. The strands are bent convergently further downward to pin 110 (located about 23 mm distally from anchoring pin 100), below which they are helically twisted about each other through two turns. The same steps are performed for neighboring strands 112 and 114. Hooks 116, 118 are also passed through hypotubes 106, 108. The respective hypotube assemblies are joined by resistance welding under an inert gas shield using about 70 ounces of force and about 10 Joules of heat.

As shown in FIGS. 4A, the process for fabricating the filtering portion includes the following steps. The previously formed anchoring portion 12 of the filter is positioned about a cylindrical portion 92 of a mandrel 93 (e.g., formed from aluminum or stainless steel), which includes a conical portion 94. The ends of strand 98 are pulled divergently downward to pins 120, 122 (located about 22 mm proximally from the distal end 123 of mandrel 91), below which the strands are helically twisted through two turns with respective ends of neighboring strands 112, 114. The ends of strand 98 are convergently pulled further downward to pin 124 (located about 8 mm proximally from the distal end 123 of mandrel 91), below which the ends of strand 98 are helically twisted about each other through about 4–7 turns to the apical distal end of the filtering portion. The resulting six pairs of helically twisted strands are passed through a short hypotube (not shown), the top of which is TIG welded to securely fix all of the strands.

A metallic wire is wrapped about the filter/mandrel assembly to tightly secure the relative positions of the elongated wire strands defining the cells in the anchoring and filtering portions. The filter and the forming mandrel are then placed in an oven set to a temperature of about 450° C. for a period of 15 to 20 minutes. Prior to this heat treatment the nitinol wires are relatively malleable, but after heat treatment the nitinol wires strands preferentially maintain their shape. Once the mandrel has cooled the anchoring pins are removed and the filter is removed from the mandrel.

Figure 5:
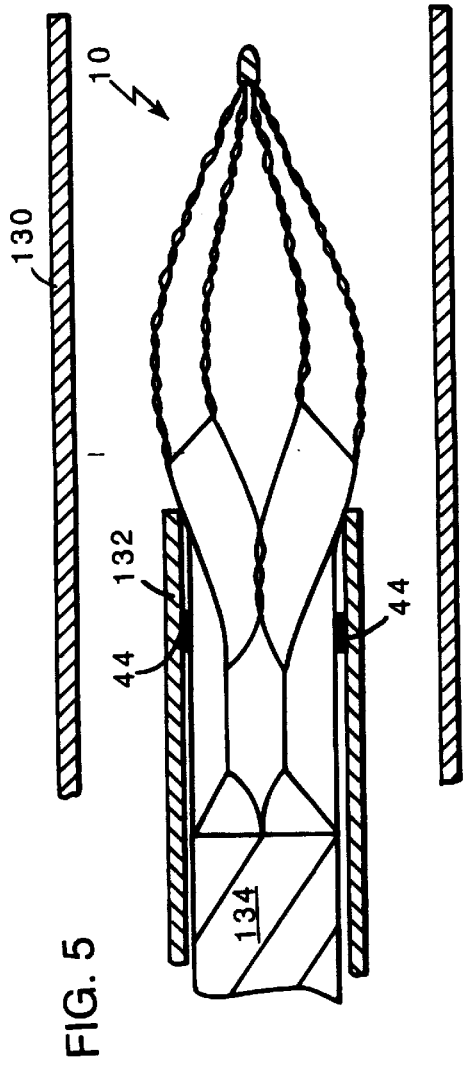
FIG. 5 is a diagrammatic side view of a filter being delivered to a blood vessel.
Figure 5A:
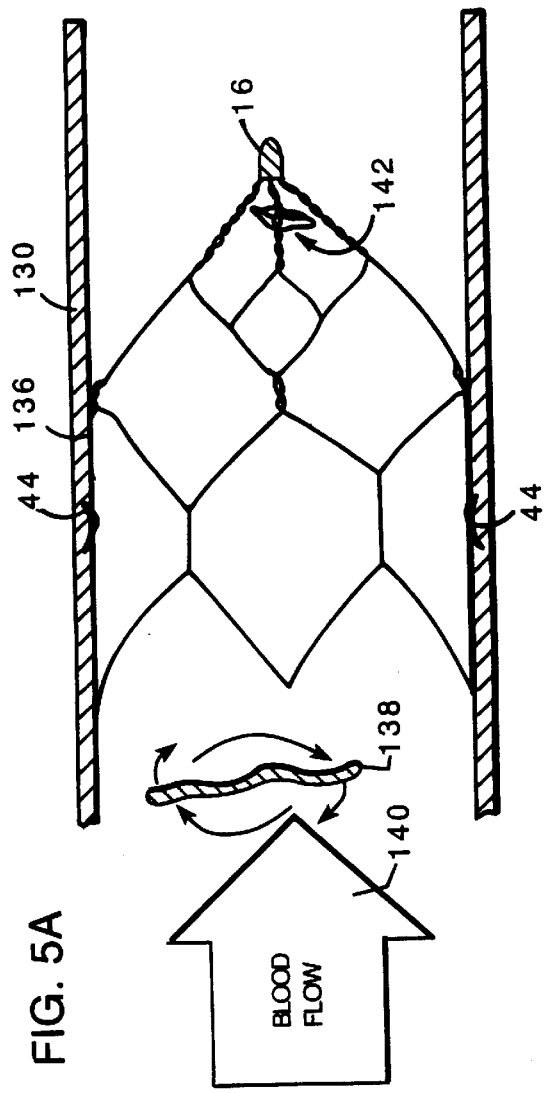
FIG. 5A is a diagrammatic side view of a filter anchored in a blood vessel.

Referring to FIGS. 5 and 5A, a blood clot filter 10 is delivered to a desired location within a vessel 130 (e.g., a vena cava having a diameter on the order of about 20 mm) through a previously inserted teflon sheath 132. Sheath 132 having an outer diameter on the order of about 3 mm is inserted percutaneously, e.g., via a small opening (on the order of 9 Fr (about 0.117 inch)) in the groin and into the femoral vein of a patient. A pusher 134, extending proximally to a location outside of the patient, is used to advance filter 10 through the sheath. Once the distal end of the sheath is properly positioned in vessel 130, pusher 134 advances filter 10 to the distal end of the sheath and holds filter 10 in the desired position in the vessel. The sheath is then pulled back, releasing the filter within vessel 130, as shown in FIG. 5A. Once the filter is released, the sheath and the pusher can be withdrawn from the patient as a single unit.

Referring to FIG. 5A, after the filter is released within vessel 130, the self-expanding cells of the anchoring portion urge the anchoring portion to outwardly expand against an inner wall surface 136 of vessel 130 with sufficient force to prevent migration of the filter through the vessel. Within sheath 132 hooks 44 lie flat and conform to the shape of the cylindrical portion to allow the filter to slide through the sheath, but when the filter is released from the sheath the hooks spring outwardly from the anchoring portion of the filter for engagement with wall surface 136. The expansion of the anchoring portion imbeds hooks 44 into the walls of the vessel to further secure the filter within the vessel.

We note that FIGS. 5 and 5A are not drawn to scale, but instead are drawn diagrammatically for purposes of illustration.

In operation, the filter captures a blood clot 138 in blood flow 140 (e.g., on the order of 1 liter per minute) by guiding the clot to the apical distal end 16 of the filtering portion. Captured clots 142 are maintained in the central region of the blood flow where the velocity is highest to achieve the most effective lysing action.

As mentioned above, the sizes of the cells in the filtering portion are selected to be small enough to capture clots of a specified size with a desired level of efficiency (e.g., with clot capturing efficiency and patency comparable to a GREENFIELD® 24 Fr stainless steel filter, available from Medi-Tech, Inc. of Watertown, Mass., U.S.A.). Thus, it is desirable to reduce the size of the cells to increase the efficiency of clot capture. However, smaller cells create greater turbulence in the blood flow, encouraging clot formation on the filter that may result in the occlusion of a vessel. A filter according to the invention minimally disturbs blood flow, while achieving a desirable level of filtering efficiency. The sizes of the cells in the filtering portion decrease the closer they are to the apical distal end 16. Thus, cell size in the filtering portion varies inversely with blood flow velocity: larger cells are positioned near the vessel walls where the flow velocity is relatively low and smaller cells are positioned in the central region of the vessel where the flow velocity is highest. Clots traveling with lower velocity do not pass through the larger size cells in the periphery of the conical filtering portion, but are instead guided to the apical distal end of the filtering portion. Clots traveling with higher velocities in the central region of the vessel, which may otherwise pass through the larger size peripheral cells, are caught in the smaller size cells located at the distal end of the filtering portion.

Figure 6B:
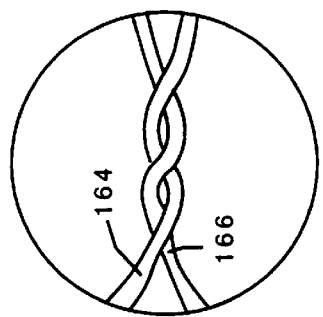
FIG. 6B is an enlarged view of a portion of the filter shown in FIG. 6.
Figure 6:
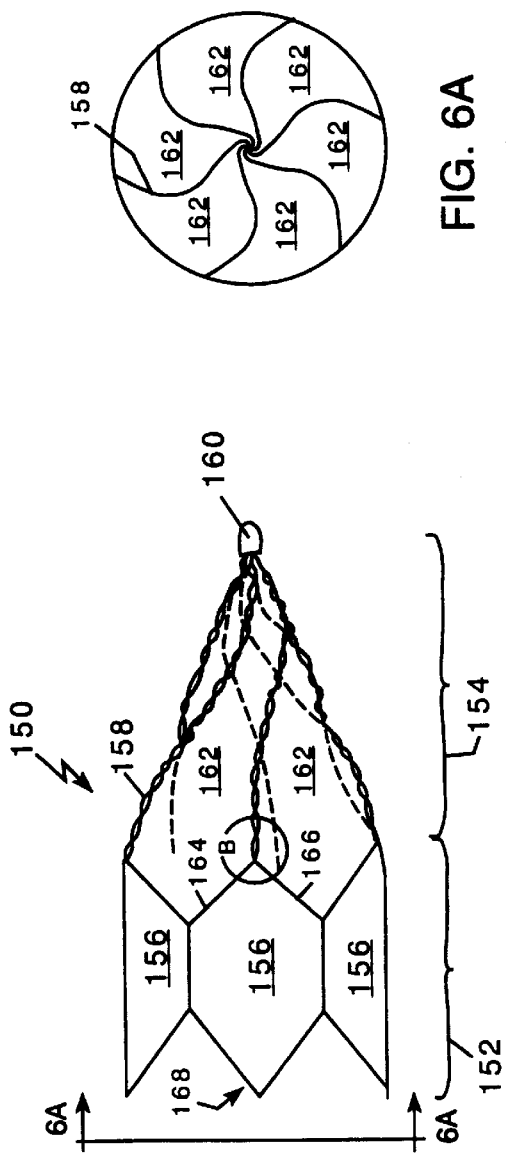

Other embodiments are also emncompassed by the invention. Referring to FIGS. 6–6B, a blood clot filter 150 includes a generally cylindrical anchoring portion 152 and a generally conical filtering portion 154. Anchoring portion 152 includes a ring of cells 156 and is constructed in a similar manner as anchoring portion 12 of filter 10, shown in FIGS. 1–1C and 2–2B. Filtering portion 154 is formed from six spirally arranged legs 158 terminating at an apical distal end 160.

Legs 158 of the filtering portion of the filter are twisted through 90° over a length of about 32–34 mm. Twisting legs 158 creates a series of spirally arranged cells 162. The projection of legs 158 in a plane transverse to the longitudinal axis of the anchoring portion reveals that the cells defined by legs 158 decrease in size from the peripheral edge of the filtering portion to the apical center; the amount of reduction being determined by the twist pitch (degrees of rotation per unit length) and the number of legs 158 in the filtering portion. This reduction in cell size achieves an advantage similar to the advantage achieved by the reduction in cell size in the embodiment of FIGS. 1–1C and 2–2B, as described above.

As shown in FIG. 6B, legs 158 are formed from pairs of elongated strands of resilient material (e.g., nitinol wire) 164, 166 helically twisted about each other. Strands 164, 166 correspond to the respective ends of strands 168 that are bent into a V-shape to form the proximal end of anchoring portion 152. Twisting strands 164, 166 increases the rigidity of legs 158 for maintaining the structural integrity of the generally conical filtering portion. Increasing the rigidity of legs 158 also prevents clots from forcing their way past the filter by displacing the relative positions of the legs.

Figure 7A:
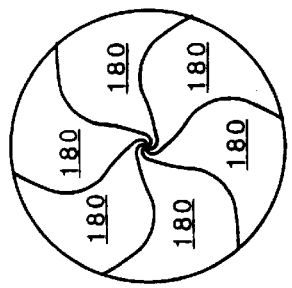
FIGS. 7 and 7A are diagrammatic side and end views of a filter.
Figure 7:
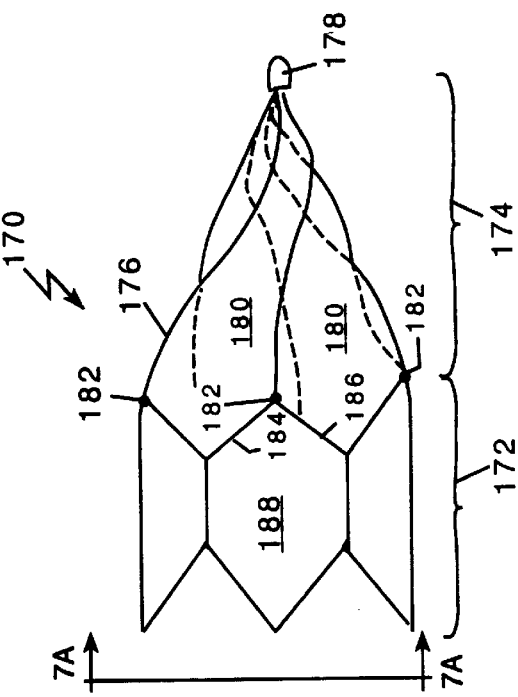

Referring to FIGS. 7-7A, in another filter embodiment 170, a generally cylindrical anchoring portion 172 is constructed in a similar manner as anchoring portion 12 of filter 10, shown in FIGS. 1–1C and 2–2B. A generally conical filtering portion 174 is formed from six spirally arranged legs 176 terminating at an apical distal end 178.

Legs 176 of filtering portion 174 are twisted through 90° over a length of about 32–34 mm, as in the filter embodiment shown in FIGS. 6–6B, creating a ring of spirally arranged cells 180. However, each leg 176 is formed from the continuation of a single elongated strand (formed from, e.g., nitinol wire) from the anchoring portion. To increase the structural integrity of the anchoring portion and the filtering portion, a series of spot welds 182 are provided at the distal end of the anchoring portion, joining strands 184, 186 that define cell 188.

Figure 8A:
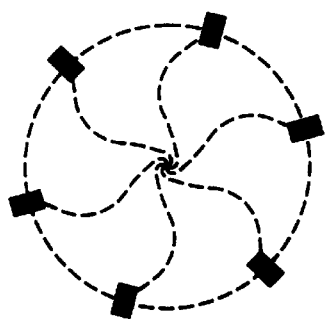
FIGS. 8A and 8B are diagrammatic end views of the filter of FIG. 8 in an expanded condition and in a compressed condition, respectively.
Figure 8B:
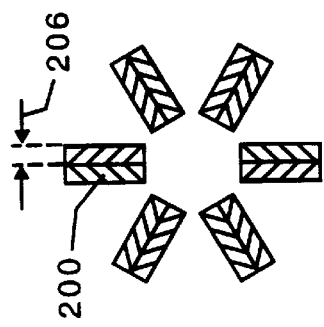
Figure 8:
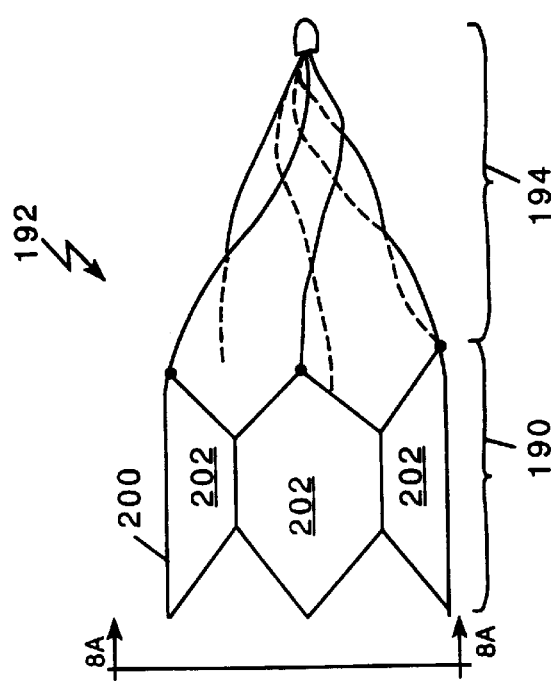
FIG. 8 is a diagrammatic side view of a filter.

As shown in FIGS. 8–8B, the anchoring portion 190 of a filter 192 may be formed from flat strands 200 (e.g., formed from superelastic material such as nitinol wire) having a rectangular cross-section. The anchoring portion of the filter is shown in an expanded condition in FIG. 8 and in a compressed condition in FIG. 8A. The flat strands are arranged in the form of a ring of cells 202 (e.g., six cells), with the number and size of the cells being selected to provide a desired level of anchoring force. The width dimension 204 (on the order of 0.5–0.7 mm wide) of flat strands 200 is oriented radially and the thickness dimension 206 (on the order of 0.05–0.15 mm thick) is oriented circumferentially. This strand orientation provides a high radial force-to-compressed profile ratio. Also, use of flat strands facilitates manufacture of the filter because there is more strand material available for welding. A filtering portion 194 (e.g., a conical filtering portion) may be formed from spirally arranged wires as shown or may be formed from rings of cells, as in the filter of FIG. 1. The filtering portion may be formed from the extension of flat strands 200. Alternatively, a filtering portion may be formed from round wire that may be joined to the flat strand anchoring portion by welding with a hypotube arranged as a universal-type hinge, or by using an adhesive or sutures.

Figure 9:
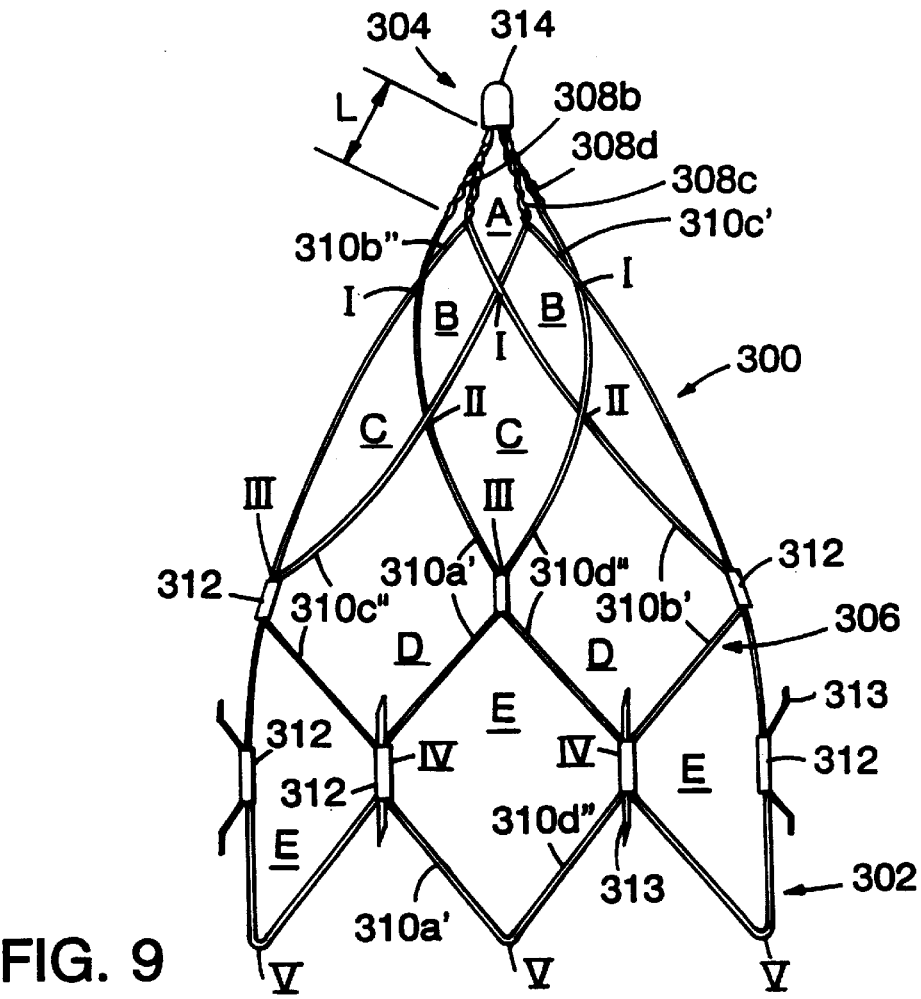
FIGS. 9 and 9A are diagrammatic side and end views of a filter in an expanded condition.
Figure 9A:
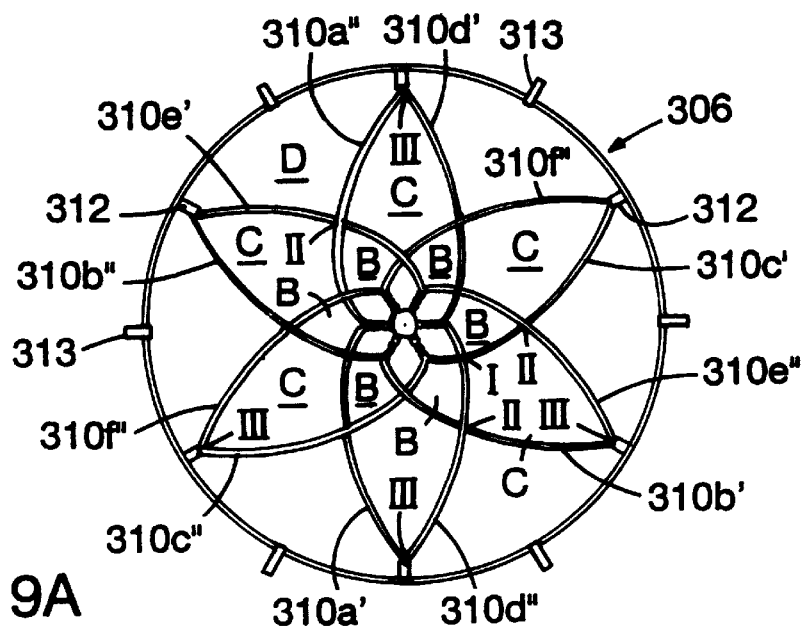

Referring now to FIGS. 9-9A, another embodiment of a self-expanding filter, illustrated in an expanded condition, includes a substantially conical-shaped filter portion 300 that has a central apex 304 at one end and is joined at its other, open end 306 to an end of a cylindrical-shaped anchoring portion 302. In the expanded condition, the open end of the filter portion is about 30–31 mm in diameter, and the filter portion has a mean length that is between about 30–40 mm.

Six pairs 308 of twisted strands 310 of resilient nitinol wire extend in a mutually twisted relationship from the apex 304 of the filter for a first distance L. Some of the strands 310 are hidden in the figures. The wire is preferably about 0.008 inches in diameter, and L can be between 0.2–0.5 inches and is preferably approximately 0.25 inches. The twisted pairs 308 diverge from each other as they spread from the center in paths substantially along the surface of an imaginary cone.

At the end of distance L, the strands 310 of each twisted pair 308 diverge from each other in opposite spirals. Strands 310, spiralling in a first sense, are indicated in FIGS. 9 and 9a by a single prime mark ', and strands spiralling in the opposite sense are indicated with a double prime mark ". The pairs of component strands 310 forming each of the twisted pairs 308 are distinguished by letters a–f.

The strands 310 continue along the surface of the imaginary cone, until adjacent strands cross each other at crossing regions, or nodes I. Each of a first ring of six open, generally diamond-shaped cells, A, is thereby defined. On two sides next to the center cells A are defined by adjacently located twisted pairs 308, and on the two more distant sides by oppositely spiralling individual strands 310 that cross at nodes I. Each cell A shares a side formed from a twisted pair 308 with an adjacent cell A.

The strands 310 cross in an overall woven relationship at nodes I. Strand 310a' crosses over strand 310b", whereas at the next laterally adjacent node I, strand 310b' crosses over strand 310c", and so on, alternating about the central axis of the filter. The woven relationship establishes a slidable engagement of the crossing strands 310, permitting the strands to slide relative each other at the nodes I during radial compression or expansion of the filter.

From nodes I the strands 310 continue in their generally spiralling relationship, progressing along the general surface of the imaginary cone. The strands 310 reach and cross further oppositely spiralling strand 310 at nodes II. The strands 310 again cross in a woven, slidable relationship such that each strand 310" that passed under a strand 310' at a node I now crosses over a different one of strands 310' at a node II.

A second ring of six open, four-sided cells B that are each larger than cells A is thus defined adjacent cells A. Each cell B shares two short sides, located closest to the apical center 304, with two adjacent cells A, and shares a node I with an adjacent cell B on each laterally spaced corner. The two short sides of each cell B are formed from strands 310 diverging from one of the twisted pairs 308. For example, strands 310a' and 310a" form two sides of one of cells B, strands 310b' and 310b" form two sides of the next adjacent cell B, and so on. Two other, longer sides of each cell B are formed from oppositely spiralling strands diverging from the next adjacent twisted pairs 308. For example, strands 310b" and 310f' form the long sides of one of cells B that has short sides formed from strands 310a' and 310a".

The strands 310 continue spiralling from nodes II until they reach joints at a third set of nodes III. A third ring of six open, four-sided cells C, each larger than cells B and A, is thus formed. A corner of each cell C closest the apical center of the filter portion is defined by one of nodes I. Two other corners farther from the apical center are formed from laterally adjacent nodes II. The fourth corner of each cell C is formed from one of nodes III. Two sides of each cell C closest to the apical center are formed by strands 310 that form adjacently located long sides of two adjacent cells B, for example strands 310c" and 310b'. Strands forming the two other long sides of the two adjacent cells B, in this instance strands 310a' and 310d", continue past nodes II to form two sides of that cell C farther from the apical center 304. While strands 310 joined at nodes III are not free to move relative to one another, strands 310 crossing at the other corners of cells C, at nodes I and II, are slidable relative to each other.

Strands 310 diverge from nodes III, although not in a spiralling fashion. For example, strands 310a' and 310d" diverge at node III and then join with strands 310c" and 310b', respectively, at nodes IV. A fourth ring of four-sided, open cells D is thereby formed, that are larger yet than cells A,B or C and lie close to parallel with the direction of flow Z. The strands forming each of cells D are fixed together where they cross at two nodes III and one node IV, but are slidable relative to each other at one node II.

The strands connecting between nodes III and IV define the open end 306 of the conical filter portion 300. These strands 310 also form a boundary for one end of the anchoring portion 302. The anchoring portion 302 is formed of a fifth ring of six diamond-shaped, open cells E, that lie along the inner wall of the blood vessel, parallel to the direction of blood flow. In the expanded configuration, the anchoring portion 302 is preferably approximately 25 mm long and approximately 30–31 mm in diameter.

Strands forming two sides of each cell D that are farthest from the apical center 304 also form sides of two adjacent cells E. The strands diverge at nodes IV and intersecting strands are joined again at nodes V. In the preferred embodiment shown in FIG. 9, for example, strands 310a' and 310d" diverge from node III, are joined to strands 310c" and 310b', respectively at adjacent nodes IV, and diverge from nodes IV and are joined again at node V, which, in this embodiment, is actually a bend in a single strand. In some applications, it may be desirable to form a longer anchoring portion by simply forming one or more additional rings of diamond-shaped, open cells that lie along the lumen wall.

Strands 310 are joined at nodes III and IV by positioning a small cylindrical sleeve 312 around a pair of strands and then by welding or crimping the sleeve 312 to the strands. The twisted pairs 308 are joined where they converge at the apex 404 by positioning a sleeve 314 over them and then welding or crimping the pairs 308 and the sleeve together.

Hooks 313 are coupled to the anchoring portion 302 at nodes IV for engaging the inner wall of a blood vessel such that the filter will not slip out of position once emplaced.

The structure of cells A, defined by the twisted pairs 308 in the region adjacent to the center 304 of the filter portion 300, achieves an open area that is relatively large in the central region of greatest blood flow rate in comparison to the case that would exist if the same number of strands 310 commenced their independent spiralling at the center of the filter unit 300. The relatively open geometry obtained by twisting the strands 310 into pairs 308 before joining them at the center 304 enhances blood flow and clot-lysing action and reduces any tendency for forming new clots on the filter.

The relatively large openings of cells A, and the progressively larger cells B, C and D, while providing a relatively low flow resistance, are small enough to capture clots effectively, given the respective aspect angles that they present to the flow.

Each filter cell A, B, C and D in this embodiment has at least one node formed by crossing strands that can slide relative to each other when the filter is radially or longitudinally deformed. Cells B and C intermediate the extremities of the conical structure have such slidable engagement at three nodes.

The strands 310 spiral in gently arcuate paths between the twisted pairs 308 and nodes III. There are no sharp bends in the strands where they cross at nodes I or II. This feature enhances the ability of the strands 310 to slide relative to each other at their crossing regions. The woven, crossing, and slidable relationship of the strands 310 at the nodes I and II in this embodiment produces a structural integrity sufficient to maintain the desired conical structure and filtering aspect, while having a degree of sliding self-adjustability when compressed or expanded that contributes to the filter's ability to conform to various size vessels.

Figure 10A:
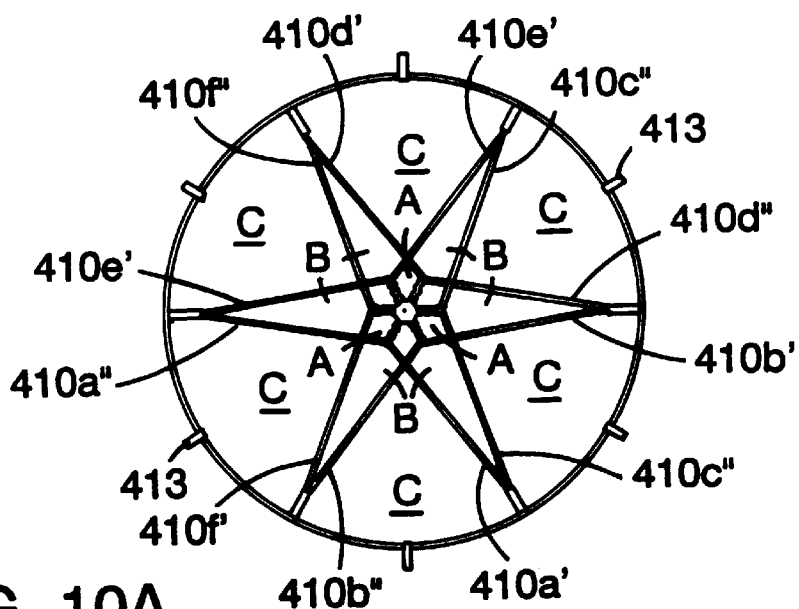
FIGS. 10 and 10A are diagrammatic side and end views of a filter in an expanded condition.
Figure 10:
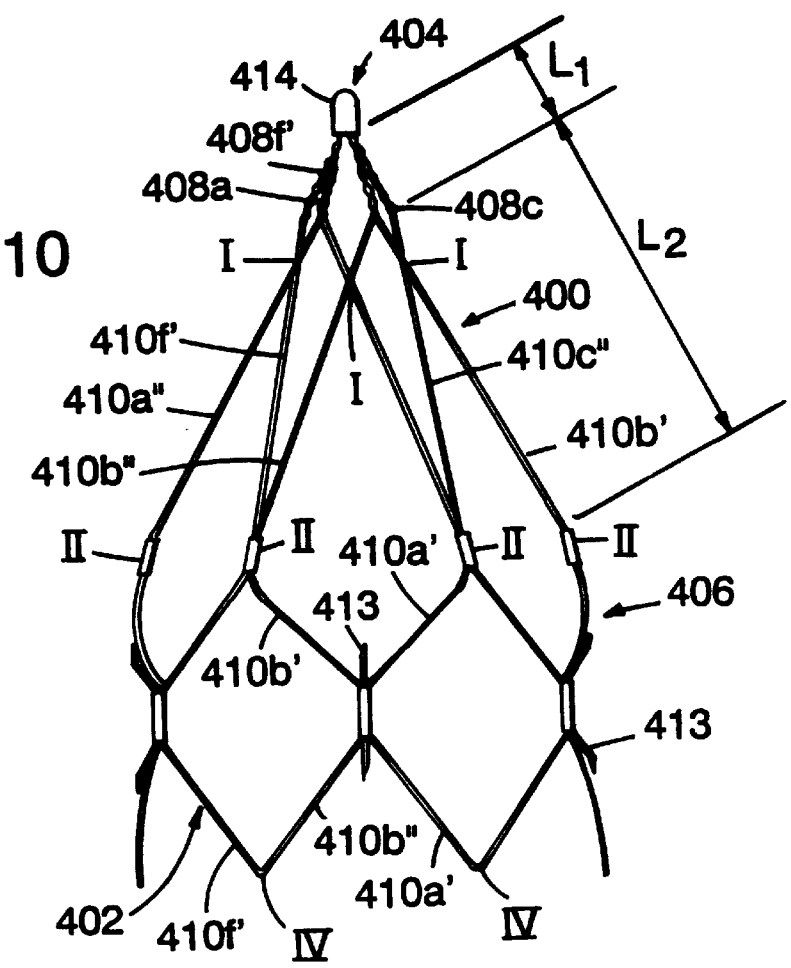

Referring now to FIGS. 10 and 10A, another embodiment of a self-expanding filter, illustrated in an expanded condition, includes a substantially conical-shaped filter portion 400 that has a central apex 404 at one end and is joined at its other, open end 406 to an end of a cylindrical-shaped anchoring portion 402. Like the filter illustrated in FIGS. 9 and 9A, this filter is about 28–30 mm in diameter in the expanded condition and the filter portion is about 30–40 mm long.

Six twisted pairs 408a–f of elongated strands 410 of nitinol wire extend from the apex for a distance $L_1$ along the surface of an imaginary cone. The strands 410 forming each twisted pair 408 then diverge from each other at an angle and continue toward the open end 406 in approximately straight paths along the surface of the imaginary cone. Some of the strands 410 and twisted pairs 408 are hidden in the figures. The strands are referenced by letters a–f to indicate the twisted pairs from which they respectively originated. $L_1$ can range between about 0.2–0.5 inches, and is preferably about 0.25 inches.

A first group of the strands 410 that diverge from the twisted pairs 408 in one direction, indicated by a single prime ', each cross under a strand 410 from an adjacent twisted pair 408 that diverges in the other direction, the second group of strands being indicated by a double prime". For example, strand 410a' crosses over strand 410b", strand 410b' crosses under strand 410c", etc. The strands 410 are slidably movable relative to each other at the crossing regions, or nodes I, during expansion and compression of the filter.

A first ring of six diamond-shaped open cells A is formed by the twisted pairs 408 and the crossing strands 410. Each cell A has two sides near the apex 404 that are formed from adjacent twisted pairs 408, and two sides farther from the apex 404 that are formed from crossing strands 410 that diverge from those two twisted pairs. For example, one of cells A is formed from twisted pairs 408a and 408b, and strand 410a' that crosses under strand 410b".

The strands 410 continue in substantially straight paths from nodes I to the open end 404 where pairs of strands are coupled together at nodes II, thereby defining a second ring of six diamond-shaped, open cells B. The distance $L_2$ between the points of divergence of the strands 310 forming the twisted pairs 308 and the nodes II is preferably approximately 1.1 inch. Each of cells B is defined on two sides nearest the apex 404 by the two strands 410 that diverge from one of the twisted pairs 408 and the two strands from adjacent twisted pairs that cross the first two strands. For example, one of cells B is formed on two sides from strands 410a' and 410a" that diverge from twisted pair 408a, and on two other sides from strands 410f" and 410b' that cross strands 410a' and 410a" respectively.

The strands 410 diverge from nodes II and are each joined, at nodes III, with a strand diverging from an adjacent node II, thereby forming a third ring of cells C adjacent the open end 406 of the filter portion 400. For example, one of cells C is formed from strands 410a' and 410b" that cross at a node I, are joined to strands 410c" and 410f' respectively at adjacent nodes II, and each diverge therefrom and are joined at a node III. Each of cells C includes only one crossing region, node I, at which the strands are slidably movable relative to each other.

The anchoring portion is formed from a fourth ring of six diamond-shaped cells D, each cell D sharing a side with each of two neighboring cells C. The same strands that diverge from a node II at one corner of each cell D again join at a node IV at an opposite corner of the cell. Adjacent nodes III form the other two corners of each cell D. For example, nodes II', III', IV' and III" form the corners of cell D', and nodes II", III", IV" and III'" form the corners of an adjacent cell D".

Filter portion 400 has one fewer ring of cells than filter 300. Cells A and C are each formed from strands forming only one crossing region I where the strands are slidably movable relative to each other. The strands or twisted pairs forming each of cells A and C are joined together at their other corners. There is only one intermediate ring of cells B, and these cells each have only two nodes I where the strands are slidably movable relative to each other.

The strands 410 diverging from the twisted pairs 408 in filter 400, like the strands 310 in filter 300, do not exhibit any sharp bends that would interfere with their ability to slide relative to each other. This feature permits a smooth transition from the compressed state to the expanded condition.

Referring now to FIGS. 11 and 11A, another embodiment of a filter intended for use in an especially large vena cava has an expanded diameter of about 40–43 mm. This embodiment is similar in most respects to the embodiment illustrated in FIGS. 10 and 10A, however, it has an extra pair of strands 510. Each coaxial ring of cells in the filter portion 500 has three coaxial rings of cells A, B, and C, and the anchor portion 502 has one ring D. Each ring includes seven cells instead of the six cells in each ring in the embodiment illustrated in FIGS. 10 and 10A.

Cells A and C each include one crossing region I of strands that are slidably movable relative to each other, and cells B each include two such crossing regions I. The strands defining cells D of the anchor portion 502, however, are joined together at their crossing regions. For example, nodes II', III', IV' and III" form the corners of cell D', and nodes II", III", IV" and III'" form the corners of an adjacent cell D".

In each of the embodiments illustrated in FIGS. 10 and 11, the strands 410, 510 are joined at nodes III and IV by positioning a small cylindrical sleeve 412, 512 around a pair of strands and then by welding or crimping the sleeve 412, 512 to the strands.

Hooks 413, 513 are coupled to the anchoring portions 402, 502 at nodes III for engaging the inner wall of a blood vessel such that the filter will not slip out of position once emplaced.

Although the invention has been described in connection with blood clot filtering in the vena cava, the present invention would also be useful for filtering clots in other areas of the vascular anatomy. For example, blood clot filtering may be useful in vessels leading to the brain. The filter used in such applications would be constructed of appropriate size and of appropriate material to provide proper anchoring force against an inner wall surface of the vessel in which the filter is disposed.

In further embodiments, the respective strands 38 and hooks 44 in regions of contact 40 (FIG. 1) in the anchoring portion of the filter may be joined together using laser welding along a length of about, e.g., 2–3 mm, instead of using a hypotube and resistance welding.

In other embodiments, the filter may be of the non-self-expanding type, preferably delivered using a catheter having an expandable balloon. The cells can be made of plastically deformable material, which may be, for example, tantalum, titanium, or stainless steel.

In still other embodiments, the filter may be formed of a temperature-sensitive shape memory material with a transition temperature around body temperature. The filter may then be delivered in a compressed condition in one crystalline state and expanded by crystalline phase transformation when exposed to body temperature.

In other embodiments, at least a portion of the filter may be formed from nitinol wire having a core of tantalum wire or other radiopaque material, as described in U.S. Ser. No. 07/861,253, filed Mar. 31, 1992 and U.S. Ser. No. 07/910,631, filed Jul. 8, 1992, both of which are herein incorporated by reference. This enhances the radiopacity of the filter so that the filter may be viewed using X-ray fluoroscopy to monitor placement and operation of the filter.

In still other embodiments, the filter may be coated with a drug for in vivo compatibility prior to delivery into the body. For example, the filter may be coated with heparin, as described in U.S. Pat. Nos. 5,135,516 and 5,304,121, which are herein incorporated by reference.

Other embodiments are within the scope of the claims.

We claim:

1. A filter sized and constructed to be compressed and passed through the vasculature of a patient to be anchored against an inner wall surface of a blood vessel for capturing blood clots in a blood stream passing therethrough, said filter comprising:

an anchoring portion comprising a generally cylindrical self-expanding body formed from resilient material, said generally cylindrical body having proximal and distal ends and defining an axial direction and having a structure of variable diameter that is expandable from a low-profile compressed condition to a larger profile expanded condition, wherein said resilient material urges said generally cylindrical body to radially expand and to thereby apply anchoring radial force against the inner wall surface of the blood vessel; and a filtering portion aligned with said generally cylindrical body, and having an open proximal end supported near the distal end of said anchoring portion, wherein the filtering portion includes elongated strands structured to provide a capture cross-section that prevents large clots from passing therethrouqh.

2. The filter of claim 1 wherein said anchoring portion and said filtering portion are substantially non-overlapping to achieve a low profile compressed condition for delivery of the filter through the vasculature.

3. The filter of claim 2, wherein said filtering portion is formed from a plurality of the elongated strands arranged to form a generally conical structure to guide blood clots in the blood stream flowing therepast to an apical distal end of said generally conical filtering portion for lysing.

4. The filter of claim 3 wherein said elongated strands are fixedly attached to one another only at the apex of said generally conical filtering portion.

5. the filter of claim 3, wherein said elongated strands define a plurality of neighboring filtering cells.

6. The filter of claim 5, wherein the cells are arranged in a plurality of coaxial rings of neighboring cells, each ring being progressively more distant from the apical distal end and having cells that are larger than the cells of the ring next closest the apical distal end.

7. The filter of claim 6, wherein neighboring filtering cells are loosely coupled together at the respective areas of contact between neighboring cells.

8. The filter any of claim 5, wherein neighboring cells are coupled together by helical twisting of portions of respective elongated strands of neighboring cells.

9. The filter of claim 7 wherein the portion of the twisted together elongated strands are capable of slight mutual separation or rotation to accommodate changes in the shapes of said cells from the expanded to the compressed conditions.

10. The filter as in any one of claims 3–6, wherein said elongated strands are spirally arranged from the proximal end of said filtering portion to the apical distal end of said filtering portion.

11. The filter of claim 3, wherein said elongated strands are selected to have sufficient rigidity to maintain the generally conical shape of said filtering portion in a flowing blood stream.

12. A filter sized and constructed to be compressed and passed through the vasculature of a patient for anchoring against an inner wall surface of a blood vessel for capturing blood clots in a blood stream passing therethrough, said filter comprising:
a cylindrical anchoring portion having proximal and distal ends and defining an axial direction and having a structure of variable size diameter expandable from a low-profile compressed condition to a larger profile expanded condition; and
a filter axially aligned with said generally cylindrical body having an open proximal end supported from the distal end of said anchoring portion and having a distal end, said filter defined by elongated spiral strands,
wherein said cylindrical anchoring portion and said filter are substantially nonoverlapping to achieve a low profile compressed condition for delivery of the filter through the vasculature.

13. A filter having a longitudinal axis, sized and constructed to be compressed and passed through the vasculature of a patient and to be expanded and anchored against an inner wall surface of a blood vessel for capturing blood clots in a blood stream passing therethrough, said filter comprising a filter portion having a closed distal end and an open proximal end, the filter portion comprising two sets of strands formed of resilient material that spiral in opposite directions in a crossing pattern that defines a plurality of open cells, the strands being slidably movable relative to each other at regions where they cross.

14. The filter of claim 13, wherein the cells are arranged in a plurality of rings of neighboring cells, each ring being progressively more distant from the distal end and having cells that are larger than the cells of the ring next closest the distal end.

15. The filter of claim 14, wherein the cells of a first ring closest to the, distal end each comprise two sides closest to the distal end that are formed of twisted pairs of the strands, and wherein the strands of each twisted pair diverge from the twisted pair in the opposite spiral directions.

16. The filter of claim 15, wherein the twisted pairs converge at the distal end.

17. The filter of claim 14, wherein the plurality of rings comprises:
a ring nearest to the, distal end, comprised of cells each including only one of the crossing regions of relatively slidable strands;
a ring nearest the open end comprised of cells each including only one of the crossing regions of relatively slidable strands; and
at least one intermediate ring comprised of cells each including only three of the crossing regions of relatively slidable strands.

18. A filter sized and constructed to be passed through the vasculature of a patient in a compressed condition and to be anchored in an expanded condition against an inner wall surface of a blood vessel for capturing blood clots in a blood stream passing therethrough, said filter including a filter portion that is substantially conical-shaped in the expanded condition and having an apical distal end and an open proximal end, the filter portion comprising two sets of strands of spring material that spiral in opposite directions in a crossing pattern, the strands being relatively slidable at regions where they cross, in the expanded condition the crossing pattern defining a plurality of four-sided, open cells, the cells being arranged in rings having a common axis, the cells of each ring being progressively larger with distance from the apical center, a first ring nearest to the apical center comprised of cells each including only one of the crossing regions of relatively slidable strands, at least one intermediate ring comprised of cells each including at least two of the crossing regions of relatively slidable strands, and a third ring nearest the open end comprised of cells each including only one of the crossing regions of relatively slidable strands, wherein the cells of the first ring each comprise two sides closest to the apical center that are formed of twisted pairs of the strands, wherein the twisted pairs join at the apical center.

19. A filter having a longitudinal axis, said filter sized and constructed to be passed through the vasculature of a patient in a radially compressed condition and to be anchored against an inner wall surface of a blood vessel in a radially expanded condition for capturing blood clots in a blood stream passing therethrough, said filter comprising a filter portion that includes a distal end, an open proximal end of variable size diameter, and elongated strands extending from the distal end to the open proximal end, the strands being twisted together in twisted groups which converge at the distal end to define common borders of a plurality of open filtering cells.

20. The filter of claim 19, wherein the twisted groups of strands are twisted pairs of strands that converge at the distal end.

21. The filter of claim 19, wherein the strands forming each of the twisted groups diverge from each other at a location between the distal end and the open proximal end and extend in paths therefrom to the open proximal end, the strands diverging from the twisted groups and the twisted groups together defining the plurality of open cells.

22. The filter of claim 21, wherein the path of each strand diverging from the twisted groups crosses the path of at least one other strand diverging from the twisted groups.

23. The filter of claim 22, wherein the strands diverging from the twisted groups are slidably movable relative to each other at regions where they cross.

24. The filter of claim 21, wherein each strand is joined to another strand at the open proximal end.

25. The filter of claim 21, wherein the cells are arranged in a plurality of rings of neighboring cells, each ring being progressively more distant from the distal end and having cells that are larger than the cells of the ring next closest the distal end.

26. The filter of claim 25, wherein the cells of a first ring nearest to the distal end and the cells of a second ring farthest from the distal end each include one crossing region wherein the strands are slidably movable relative to each other, and wherein the cells of a third ring between the first and second rings each include at least two crossing regions wherein the strands are slidably movable relative to each other.

27. The filter of claim 25, wherein each ring comprises at least six cells.

28. The filter of claim 21, wherein the paths of the strands that diverge from the twisted groups are substantially straight.

29. The filter of claim 21, wherein the paths of the strands that diverge from each of the twisted groups spiral in different directions.

30. A filter sized and constructed to be passed through the vasculature of a patient in a compressed condition and to be anchored in an expanded condition against an inner wall surface of a blood vessel for capturing blood clots in a blood stream passing therethrough, said filter including a filter portion that is substantially conical-shaped in the expanded condition, an apical distal end and an open proximal end, the filter portion comprising strands that extend from an open proximal end of the filter portion to an apical distal end, pairs of the strands forming twisted pairs that converge at the apical distal end, each of the strands forming each twisted pair diverging from the twisted pair near the apical distal end and extending therefrom in an approximately straight path that crosses a strand from a neighboring twisted pair, each strand being joined to another strand at the open proximal end, the crossing strands being relatively slidable at regions where they cross, in the expanded condition the crossing strands and the twisted pairs defining a plurality of four-sided, open cells, the cells being arranged in coaxial rings, the cells of each ring being progressively larger with distance from the apical distal end, the cells of a first ring nearest to the apical distal end and the cells of a second ring nearest the open proximal end each including only one of the crossing regions of relatively slidable strands, and the cells of an intermediate third ring each including two of the crossing regions of relatively slidable strands.

31. The filter as in any one of claims 3, 13, 18, 19 or 30, wherein the strands are formed from a member of the group consisting of nitinol, a temperature-sensitive shape memory material having a transition temperature around body temperature, a plastically deformable material, and an elastic material having a core formed from a radiopaque material.

32. The filter as in any one of claims 3, 13, 18, 19 or 30, wherein the strands form a woven pattern such that the strands are slidably movable relative to each other at their crossing regions.

33. The filter as in any one of claims 13, 18, 19 or 30, comprising an anchoring portion supporting the open proximal end of the filter portion, the anchoring portion comprising a self-expansible, substantially cylindrical-shaped body axially aligned with the filter portion, formed of a resilient material that urges the self-expansible body to radially expand and apply anchoring radial force against the inner wall surface of the blood vessel.

34. The filter as in either claim 1 or 12, wherein said self-expanding anchoring portion comprises a ring of neighboring cells.

35. The filter of claim 34, wherein the cells of said anchoring portion are self-expanding.

36. The filter of claim 34, wherein the neighboring cells of the anchoring portion are fixedly coupled together at respective areas of contact.

37. The filter of claim 34, the cells of said anchoring portion are formed from one or more resilient elongated strands.

38. The filter of claim 34, when the cylindrical body is in a compressed condition said cells of the anchoring portion are elongated in the axial direction.

39. The filter of claim 33, wherein one or more hooks are fixedly coupled to said anchoring portion, the one or more hooks being formed from compliant material having an original shape that bends under a stress and that returns to its original shape when the stress is removed, said one or more hooks respectively projecting from said anchoring portion at an acute angle with respect to the axial direction for engagement with a vessel wall, said one or more hooks further being deflectable toward said anchoring portion for achieving a low-profile.

40. The filter of claim 39, wherein said one or more hooks are formed from nitinol.

41. The filter of claim 39, wherein said one or more hooks preferentially bend toward and away from said vessel wall engaging portion.

42. The filter of claim 39, wherein said one or more hooks are formed from flat nitinol wire having a width dimension and having a thickness dimension substantially smaller than said width dimension for achieving preferential bending, said flat nitinol wire being oriented so that the thickness dimension of said flat nitinol wire coincides with a radial direction of the anchoring portion.

43. The filter of claim 34, wherein the strands extend beyond the open proximal end to form the body of the anchor portion.

44. The filter as in any one of claims 1, 12, 13, 18, 19, or 30, wherein said filter is coated with a drug for beneficial physiological effect.

45. The filter of claim 44, wherein the drug improves in vivo capability.

\* \* \* \* \*